US010500036B2

(12) United States Patent
Kassab (10) Patent No.: US 10,500,036 B2
(45) Date of Patent: *Dec. 10, 2019

(54) TISSUE ENGINEERING OF BLOOD VESSELS

(71) Applicant: DTherapeutics, LLC, San Diego, CA (US)

(72) Inventor: Ghassan S. Kassab, La Jolla, CA (US)

(73) Assignee: DTherapeutics, LLC, San Diego, CA (US)

( * ) Notice: Subject to any disclaimer, the term of this patent is extended or adjusted under 35 U.S.C. 154(b) by 97 days.

This patent is subject to a terminal disclaimer.

(21) Appl. No.: 14/935,928

(22) Filed: Nov. 9, 2015

(65) Prior Publication Data

US 2016/0128825 A1  May 12, 2016

Related U.S. Application Data

(63) Continuation of application No. 11/919,533, filed as application No. PCT/US2006/016522 on May 1, 2006, now Pat. No. 9,179,996.

(Continued)

(51) Int. Cl.
*A61F 2/06* (2013.01)

(52) U.S. Cl.
CPC ............... *A61F 2/06* (2013.01); *A61F 2/062* (2013.01); *A61F 2250/003* (2013.01)

(58) Field of Classification Search
CPC ........ A61F 2210/0004; A61F 2250/003; A61F 2/062; A61F 2/88; A61F 2250/0015; A61F 2/0031; A61L 27/56
See application file for complete search history.

(56) References Cited

U.S. PATENT DOCUMENTS

| 3,726,279 A | 4/1973 | Barefoot et al. |
| 4,865,031 A | 9/1989 | O'Keeffe |

(Continued)

FOREIGN PATENT DOCUMENTS

| DE | 3830481 A | 3/1990 | |
| WO | WO 2005057165 A2 * | 6/2005 | ........... A61B 17/866 |

OTHER PUBLICATIONS

International Searching Authority, International Search Report, PCT/US06/16522 dated Apr. 29, 2008.

(Continued)

*Primary Examiner* — Brian E Pellegrino
(74) *Attorney, Agent, or Firm* — Reichel Stohry Dean LLP; Mark C. Reichel; Natalie J. Dean (57) ABSTRACT

Method and apparatus for mapping the shape and dimensions of a 3-dimensional body, by applying to the 3-dimensional body a stretchable covering configured and dimensioned such that in its stretched condition it tightly engages and conforms to the shape and dimensions of the 3-dimensional body to be mapped. The stretchable covering carries a plurality of reference devices, such as bands and/or markers which are at know or determinable reference locations in an initial condition of the covering, and which change their locations in the stretched condition of the stretchable covering according to the shape and dimensions of the 3-dimensional body covered thereby. The locations of the markers on the stretchable covering are determined after the stretchable covering has been applied to the 3-dimensional body, and are utilized to produce a map of the shape and dimensions of the 3-dimensional body.

16 Claims, 4 Drawing Sheets

Related U.S. Application Data

(60) Provisional application No. 60/675,903, filed on Apr. 29, 2005.

(56) References Cited

U.S. PATENT DOCUMENTS

| | | | |
|---|---|---|---|
| 4,870,966 A | | 10/1989 | Dellon et al. |
| 5,236,447 A | * | 8/1993 | Kubo ................. A61F 2/06 |
| | | | 623/1.39 |
| 5,500,013 A | | 3/1996 | Buscemi et al. |
| 5,633,002 A | | 5/1997 | Stricker et al. |
| 5,741,283 A | | 4/1998 | Fahy |
| 5,788,979 A | | 8/1998 | Alt et al. |
| 6,004,356 A | | 12/1999 | Wolff et al. |
| 6,031,148 A | | 2/2000 | Hayes et al. |
| 6,113,640 A | | 9/2000 | Tormala et al. |
| 6,319,264 B1 | * | 11/2001 | Tormala ............ A61F 2/0063 |
| | | | 606/151 |
| 6,458,140 B2 | | 10/2002 | Akin et al. |
| 6,726,696 B1 | | 4/2004 | Houser et al. |
| 6,730,016 B1 | | 5/2004 | Cox et al. |
| 9,179,996 B2 | * | 11/2015 | Kassab ................ A61F 2/062 |
| 2002/0143385 A1 | | 10/2002 | Yang |
| 2005/0043783 A1 | * | 2/2005 | Amis .................. A61F 2/88 |
| | | | 623/1.22 |
| 2005/0113849 A1 | | 5/2005 | Popadiuk et al. |
| 2006/0009835 A1 | * | 1/2006 | Osborne .............. A61F 2/07 |
| | | | 623/1.13 |

OTHER PUBLICATIONS

International Searching Authority, Written Opinion of the International Searching Authority, PCT/US06/16522 dated Apr. 29, 2008.

* cited by examiner

TISSUE ENGINEERING OF BLOOD VESSELS

PRIORITY

This application is related to, claims the priority benefit of, and is a continuation patent application of, U.S. Nonprovisional Patent Application Ser. No. 11/919,533, filed Oct. 29, 2007, which is related to, claims the priority benefit of, and is a U.S. § 371 National Stage Patent Application of, International Patent Application Ser. No. PCT/US2006/016522, filed May 1, 2006, which is related to, and claims the priority benefit of, U.S. Provisional Patent Application Ser. No. 60/675,903, filed Apr. 29, 2005, the contents of which are hereby incorporated by reference in its entirety into this disclosure.

BACKGROUND OF THE INVENTION

Field of the Invention

The present invention relates to tissue engineering of blood vessels. More particularly, the present invention relates to tissue engineering of an artery from a vein through control of vessel wall stress and strain.

Background of the Invention

Coronary artery bypass graft (CABG) is currently the most common surgical procedure to re-supply nutrients to a poorly perfused heart region typically through use of an existing patient blood vessel. Among the blood vessels used for CABG, the saphenous vein is the most often used because it can easily be harvested without detrimental effects due to the abundance of redundancy in the drainage system of the superficial veins. However, after implantation, approximately 10-20% of the saphenous vein grafts (SVGs) occlude after one year due to thrombotic occlusion and intimal hyperplasia, and about 50% fail after 10 years. Various attempts have been made to improve the compatibility of SVGs, including the use of anti-platelet agents, calcium channel antagonists, immuno-suppression with cyclosporine, photodynamic therapy employing laser light and gene therapy. Although these procedures do provide some short-term vessel patency, they do not confer long-term prevention of neointimal formation and remain largely experimental.

Thus, a need exists in the art for an alternative to the conventional methods of vein grafting such that the short and long-term prognosis of the procedure results in increased patient success rate and decreased re-occlusion rates. Such alternative should be universally applicable, be easy to use and be easily manufactured to apply to a large market.

SUMMARY OF THE INVENTION

This present invention provides an alternative and enhancement to conventional treatments for coronary artery disease (CAD) as well as other blood vessel conditions where an occlusion has caused a decrease in blood flow therethrough, resulting in immediate or inherent ischemic conditions. The present invention uses the findings that an increase in interior blood pressure allows the thickening of a vessel wall, or "arterialization." Through use of unique devices, systems and methods, the present invention induces an arterialization of a desired blood vessel of the venous system, such as the saphenous vein, through a gradual and minimally-shocking manner so that the venous blood vessel is allowed to gradually accept and structurally react to the increased blood pressure in its new arterial position, thereby making such substitution of the blood vessel into an arterial role much less traumatic than conventional methods.

In other exemplary embodiments, methods are disclosed to bypass an occluded region in a coronary artery without need to unnecessarily shock the replacement vein, thereby reducing the incidence of endothelial injury and, hence, resulting in enhanced survival rates.

In the exemplary embodiments of the present invention, a multi-layered or multi-component sheath is placed around a desired blood vessel to secure the structural integrity of the blood vessel as it withstands the higher pressures of its new translocated position. The sheath is designed such that it sheds layers or components in sequence to allow the wrapped blood vessel to gradually expand and re-orient itself in reaction to the interior lumen blood pressure. In time, the sheath may completely dissolve wherein the blood vessel should have been conditioned to the environment of its new location so as to now incur a pressure shock.

In one exemplary embodiment, the present invention is a device for re-engineering of blood vessels. The device includes a tubular structure for surrounding a blood vessel in a body, the tubular structure being composed of a material having multiple components, wherein each component has a resorption rate that is different than other components; and wherein as each component resorbs in the body, the blood vessel is allowed to expand to the limits allowed by the remaining components and reengineer itself according to the pressure within the blood vessel.

In another exemplary embodiment, the present invention is a sheath for arterialization of venous blood vessels in an animal body. The sheath includes a substantially tubular structure for surrounding a venous blood vessel in a body, the tubular structure including a material having multiple components of different resorption rates; and wherein as each component resorbs in the body, the venous blood vessel expands to the limit allowed by the remaining components and further arterializes.

In yet another exemplary embodiment of the present invention, a method is disclosed for re-engineering of a blood vessel. The method includes introducing a sheath around an outer surface of a blood vessel; wherein the sheath comprises a substantially tubular structure including multiple components of different resorption rates; and allowing the blood vessel to reengineer itself in response to the sheath by expanding to the limit allowed by the remaining components as each component resorbs in the body.

DETAILED DESCRIPTION OF THE INVENTION

The many advantages of the present invention are gleaned by first considering the cause of SVG failure from an engineering perspective. Arteries and veins are different structurally and hence functionally. Functionally, arteries are adapted to higher pressure while the veins experience much lower pressures. Veins also contain valves that inhibit back flow of blood. In addition, a 45-fold difference exists between the vascular compliances of arteries and veins (2.5 mL/mmHg and 120 mL/mmHg, respectively), thus, meaning that veins are much more compliant to the pressures that they encounter while arteries are relatively non-compliant to such pressures.

Structurally, both arteries and veins contain three basic layers: tunica intima, tunica media, and tunica adventitia. However, differences in thickness and composition exist across all three layers. The most evident difference is the thicker tunica media layer in arteries that enable them to withstand the significantly higher pressure. After implantation into the arterial circulation, SVGs are immediately exposed to an increase in flow and pulsatile wall shear stress. SVGs also need to adapt to significantly higher tangential and axial wall stresses and strains.

Thus, the present invention provides devices, systems and methods for addressing some of the problems associated with conventional methods of bypassing arterial occlusions using, for example, SVG. The problems that are common in such operations include the need for repeated operations, the relatively high frequency of further medical conditions or mortality resulting from the shock of the venous system to arterial pressure, and other drawbacks known to one having ordinary skill in the art.

Part of the basis for the devices, systems and methods according to the present invention is to take advantage of the findings that blood vessels do have the ability to change from one form to another depending on the type of pressure to which they are exposed. However, the present invention also attempts to at least minimize if not eliminate the problems and drawbacks with conventional step- or rapid-exposure methods of exposing a vein to arterial pressure by creating a graded or gradual-increase in arterialization of the vein.

Thus, systems and methods according to the present invention create an external body environment for the vein that results in a gradual increase and re-structuring of the blood vessel wall to levels that can withstand arterial blood pressures. Thus, any risks of shock or disintegration of the blood vessel wall because of conventional exposure to a step-increase in blood pressure is minimized or avoided. Various devices, systems and methods are introduced herein that have the ability to create a gradual tissue re-engineering in the vein such that it is conditioned to withstand the pressures that are withstood by arterial vessels in the same location. Although certain exemplary embodiments of the invention are shown, the invention is not limited to these mere examples, and has a scope beyond the examples shown herein, to all devices, systems and methods that have the capability of producing a graded increase in arterialization of a blood vessel, resulting in a gradual transformation of blood vessel wall architecture and thickness from that of vein or venule to a more arterial-like vessel.

In order to proceed in this blood vessel transformation, it is hypothesized that the in vivo vessel exists in a state of mechanical homeostasis. A small change in the mechanical environment can be physiologically tolerated by the vessel wall through structural and mechanical remodeling that restores the mechanical homeostasis or set point of the blood vessel. A large perturbation, however, can lead to pathological changes which could eventually lead to stenosis. An example of a large perturbation in the circumferential stress is the use of an SVG as an artery. Here, the rationale is to increase the stress in the wall gradually thorough a continuous, deliberate and tempered resorbing external stent or sheath.

In an unstented vein graft, the stress increase is large and very sudden (as a step function). This large stress increase stimulates an injury response that includes overly proliferative smooth muscle cells which in turn give rise to neointima formation as revealed by proliferating cell nuclear antigen (PCNA) in the media rather than in the neointima in unstented grafts. This injury-induced phenomenon, however, is subsided in vein grafts protected with a sheath according to the present invention. Another mediator known to be down regulated in vein grafts with an external sheath of the present invention is platelet-derived growth factor (PDGF). Studies have associated decreased PDGF expression with reduced medial and neointimal thickening in SVG with an external sheath in porcine.

The resorbable stent according to the present invention improves the patency of the venous graft (VG). Exemplary embodiments include an external stent material that resorbs at different rates, e.g., shows a gradient of resorption. Hence, the material changes its compliance with time. In the process, it gradually transfers the stress and strain from the stent to the VG vessel wall as it allows the graft time to gradually arterialize.

Figure 1A:
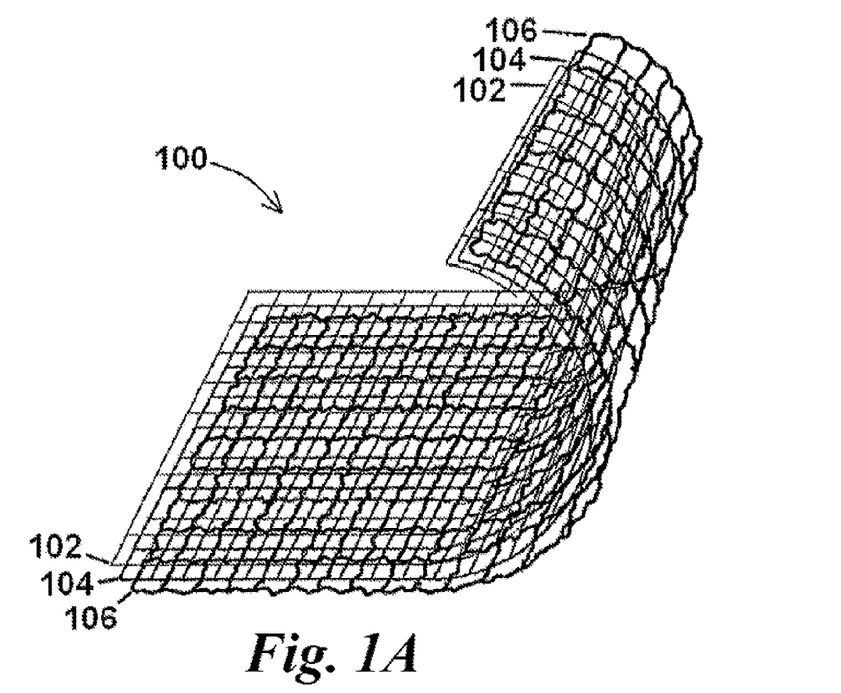
FIG. 1A shows an exemplary embodiment of the present invention as a sheet of material having multiple layers of different resorption rates.
Figure 1B:
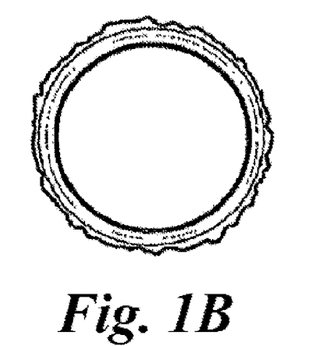
FIG. 1B shows the sheet of material according to the exemplary embodiment shown in FIG. 1A in a cross-section of a tubular shape as it would be wrapped around a blood vessel with the highest resorption rate material positioned as the most interior layer of the tube.
Figure 1C:
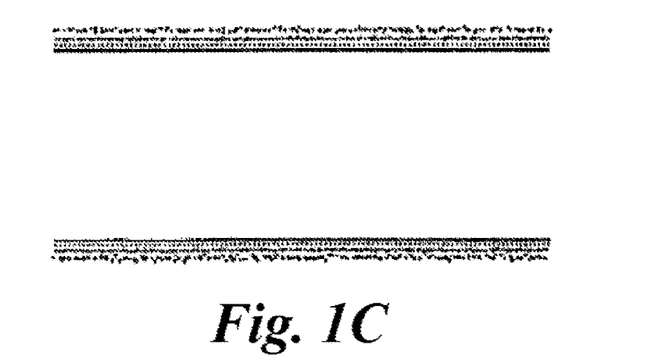
FIG. 1C shows a longitudinal cross-section of the tubular sheath of the exemplary embodiment of FIG. 1B as it would appear wrapped around a blood vessel, with the highest resorption rate material positioned as the most interior layer of the tube.
Figure 2:
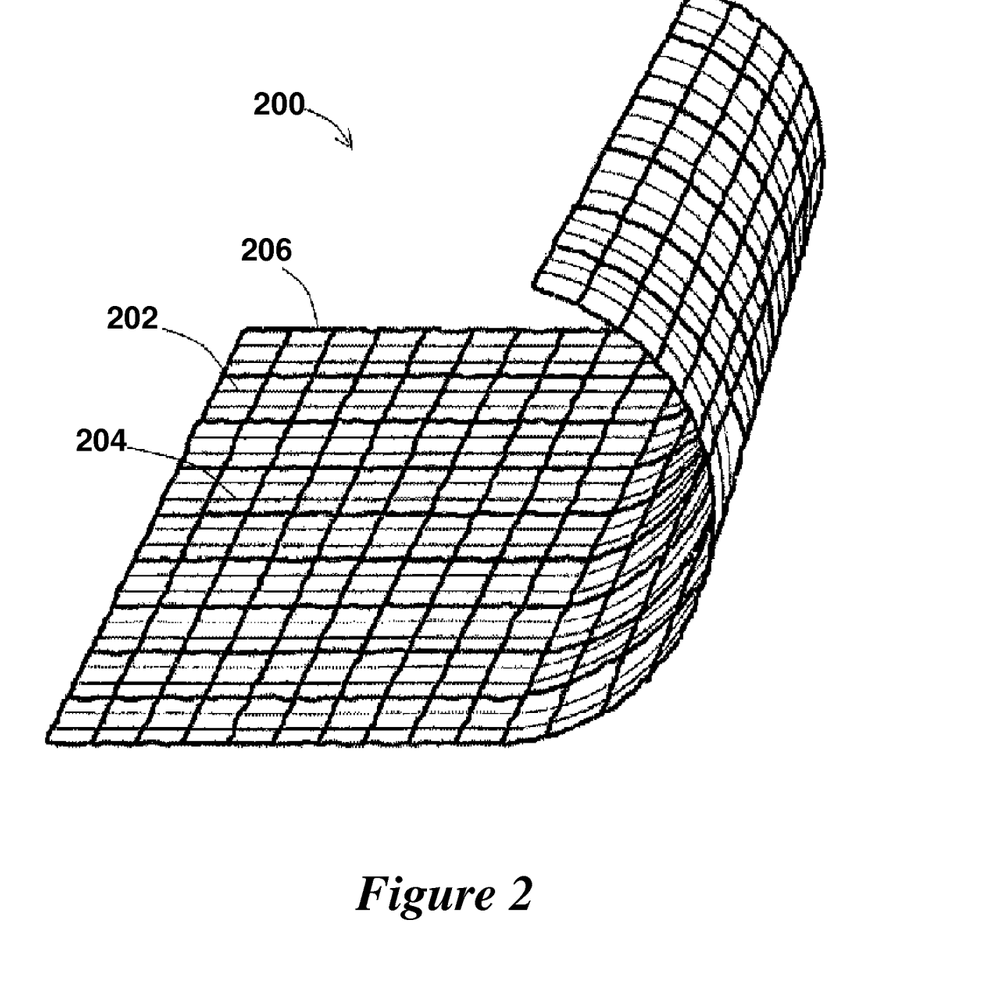
FIG. 2 shows another exemplary sheet according to the present invention that contains multiple materials interwoven together to form a single sheet, wherein each material has a different resorption rate.

Two non-limiting exemplary embodiments of the sheath or stent according to the present invention are shown in FIGS. 1 and 2. In FIG. 1, the material of sheath 100 includes multiple layers (3 layers shown in the figure, namely 102, 104, and 106), each with a different resorption rate. The resorption rate of each layer is proportional to the thickness of the fibers used therein, e.g., the thinnest fibers resorb first. The innermost layer 102 (closest to the VG wall) could include straight fibers that limit the compliance of the stent but resorb at the fastest rate. Once this layer resorbs, the next layer 104 allows for the expansion of the stent because of its more wavy structure. This layer resorbs next in a similar manner as described above and allows further expansion of the stent because of increased waviness of the third layer 106. The third layer 106 finally resorbs transferring the entire load to the vessel wall. In this procedure as outlined above, the load is gradually transferred to the VG while it arterializes.

FIG. 2 shows a similar concept with a single layer sheath 200 that incorporates fibers 202, 204, and 206 of different resorption rate in an interwoven network. The major scaffold comprising fibers 206 (thickest lines) is the most distensible and resorbs at the slowest rate. Its compliance is limited, however, by the cross-connections of two different fibers

204, 206 (different thickness). As the thinner fibers resorb first, they allow the expansion of the scaffold and hence an increase in the compliance of the external stent and so on. All three fibers 202, 204, 206 are exposed to the same internal environment and all thus begin resorption at the same time. However, the differences in resorption rate is what allows one fiber to dissolve or resorb faster than another and allows for the device as a whole to slowly allow the venous graft wall to expand out and restructure itself in response to the interior lumen pressure.

Other structures are possible as long as they also contain some combination of fibers that resorb at various rates allowing the wall of vessel graft to slowly and deliberately take on larger loads induced by the blood pressure within the graft. As this slow and methodical "bulking" of the blood vessel progresses, the material in the sheath is resorbed such that no further outside manipulation is needed to induce, accelerate or progress such blood vessel conditioning. In essence, the device, system and method are designed to operate on their own after the initial introduction into the body, independent of any further manipulation by a surgeon or other health care worker.

Various materials or combination of materials may be used for the devices and methods described according to the present invention. The most suitable materials would be ones that are biocompatible, flexible and resorbable. Certain biocomatible polymers or combinations thereof would be preferred. For example, poly-lactic-co-glycolic acid (PLGA) is a biodegradable copolymer that when degraded, gives rise to lactic and glycolic acid normally found in the body. By adjusting the ratio of lactic and glycolic acid, the degradation or resorption rate of PLGA can be manipulated. It has been shown that a loosely-fitted macroporous sheath is optimal for neointima prevention. These criteria enable fluid transfer and thus infiltration of necessary nutrient and cell types. The "variable compliance" design is implemented in a porous material that allows transport. After implantation, the sheath "zips" open gradually (3-4 weeks), stimulating a gradual increase in VG wall stress and strain and hence leading to arterialization of the graft. Exemplary embodiments of the present invention include thin yet strong PLGA sheaths so that the amount of glycolic and lactic released is minimized and, optionally, include the incorporation of fibrin.

Preparing and inserting an exemplary sheath according to the present invention may be carried out in a number of different ways as known to one having ordinary skill in the art after considering the present disclosure. One particular example that shows the benefits of a sheathed vein versus a non-sheathed vein is described herein. A left saphenous vein of 5 cm length is harvested from a porcine model. All side branches are ligated with a 6-0 suture and the segment is rinsed and stored in a saline solution containing 2 IU/mL heparin and 50 ug/ml glyceryl trinitrate at room temperature (23° C.) until graft. A right saphenous vein from the same animal serves as a sham control. A 4 cm segment of the common carotid artery is excised and grafted with the SVG. A standard end-to-end anastomoses is performed between the beveled ends (45° angle) of the vessels using 7-O sutures.

The proximal anastomoses is performed first, de-aired, and the sheath inserted for the experimental group before suturing of the distal end. Alternatively, the external sheath may be wrapped around the vein graft after the anastomoses is completed. Prior to surgery, in vitro pressure-diameter experiments are done on the SVG to determine the appropriate size of the sheath. Since the vein is very distensible at lower pressure, the sheath should be sized to match the diameter of the vein at 20-30 mmHg. After the proper size is determined, the sheath is wrapped around the vein and secured thereabout using a suture or other similar securing devices as known to one having ordinary skill in the art.

At a later predetermined time, the grafts are removed, pressure-fixed ex vivo at 100 mm Hg for 10 min using 10% formalin in 0.1 mol/L sodium phosphate buffer, pH 7.3. They are then post-fixed in the same solution for approximately 24 h, dehydrated and cleared before being processed for paraffin embedding. Transverse (5 um) sections are cut at four different levels, mounted on glass slides and stained. Mean values for all section of each graft are calculated, and average intimal, medial and vessel wall thickness are determined from the area and perimeter data. Immunostaining for PCNA and PDGF may also be conducted. Results show that the wall thicknesses and architecture of veins that underwent the procedure according to the present invention, as compared to sham controls that were not wrapped with sheaths, were more in line with what would be expected from the corresponding arterial blood vessels which such veins had replaced.

The external sheath may be constructed from a variety of materials, as known to one having ordinary skill in the art after consideration of the present invention. In one particular example, the following steps may be used to devise the composition of the external sheath. First, a sieve is conducted using a sorter for salt of the proper size. Then 0.8 g of PLGA (Birmingham Polymers, Ala.) of various ratios is dissolved in 8 mL of tetra-hydro-fluorine (THF) in different closed containers and mixed for 24 hours. In a mold lined with aluminum foil, salt is placed as a layer and then PLGA/THF mixture is poured in the mold. THF is allowed to be dried in a fume hood. Deionized water is added to dissolve the salt to create a porous polymer. At this step, a little alcohol can be added to make PLGA softer (it is usually hard and brittle when dried). Both sides of the PLGA slices may be exposed to UV for 30 minutes. Then, a toothpick may be dipped into the THF to make the layers of material having different ratios of PLGA stick together to form a tubular structure (may also use a mold). Finally, the PLGA may be wrapped in an external layer of knitted Vicryl mesh (Ethicon) so that the sheath can be sutured onto the vein graft. Other steps and procedures may also be followed to develop a suitable material for the devices according to the present invention.

In yet another exemplary procedure, PLGA of different lactic to glycolic acid ratios (50/50%, 65/35%, 75/25%) are dissolved in chloroform at 14% (w/v) overnight individually. The estimated degradation times are 1.5, 3.5, and 4.5 months respectively. The 0.5 g of 250-500 μm diameter salt particles are spread evenly onto one-layer of a 5 cm by 2 cm area covered by aluminum foil. After adding 1 mL of 14% (w/v) PLGA to the salt, PLGA is left to dry overnight. After 24 hours, PLGA sheets are immersed in deionized water for one day, and one sheet of 0.5 mm thick PLGA can be peeled off easily. A sheet of 50/50 PLGA is then wrapped around a Teflon rod with the appropriate diameter (4.8 mm or 3.2 mm), and stuck together with the application of chloroform to form a cylindrical sheath. Similarly, a second sheet of 65/35 PLGA is then wrapped around the first and a third sheet of 7525 PLGA wrapped around the second. In this way, an external sheath including three different resorption rates is obtained.

Figure 3A:
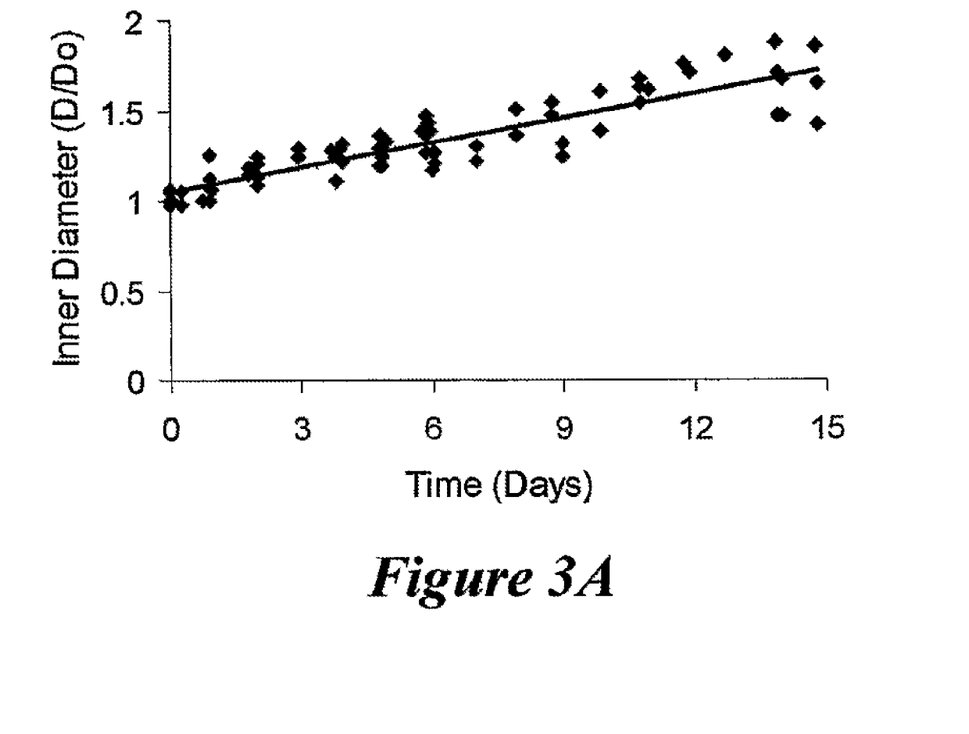
FIGS. 3A and 3B show a temporal change of the inner and outer diameters, respectively, of an exemplary sheath according to the present invention.
Figure 3B:
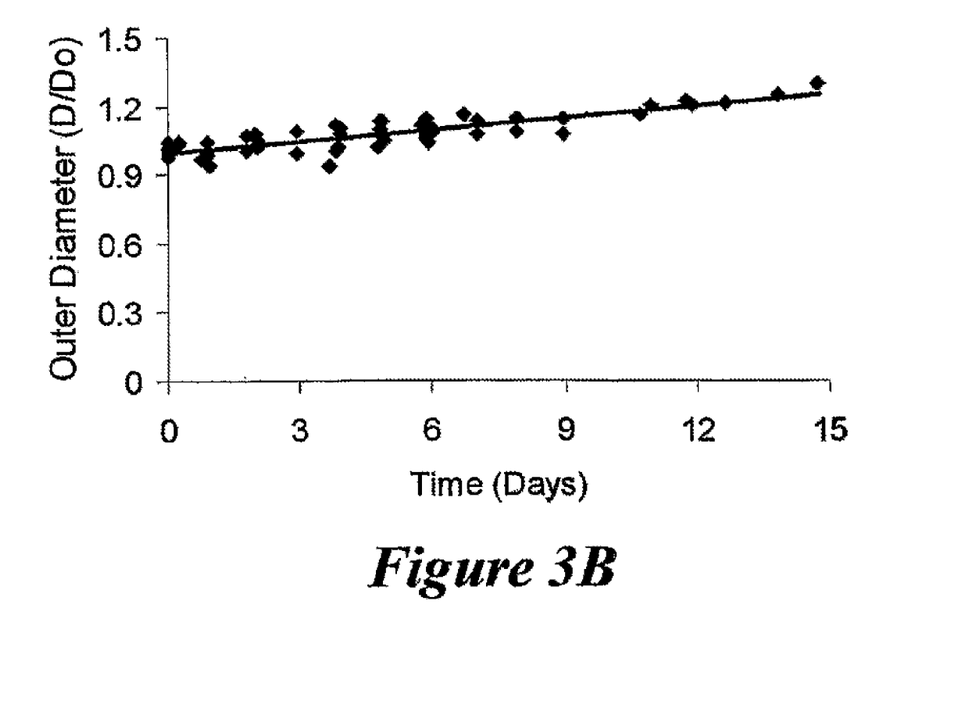

FIGS. 3A and 3B show a temporal change of the inner and outer diameters of the three-layer resorbable sheath, respectively. Each diameter is normalized with respect to the initial (Do) diameter. There appears to be a linear variation of inner and outer diameters. Consequently, the wall thickness of the scaffold decreases linearly with time. Since the variation in the geometric parameters is linear, the engineering of this material may be controlled through two parameters: the slope and the intercept. The latter dictates the initial diameter of the scaffold which depends on the size of the graft of interest. The former dictates the rate of resorption or transfer of stress and strain from the scaffold to the vein. The slope and intercept can be engineered based on the composition of PLGA used. Thus, one having ordinary skill in the art would be able to choose the proper variables that would result in a desired end-product material.

Figure 4:
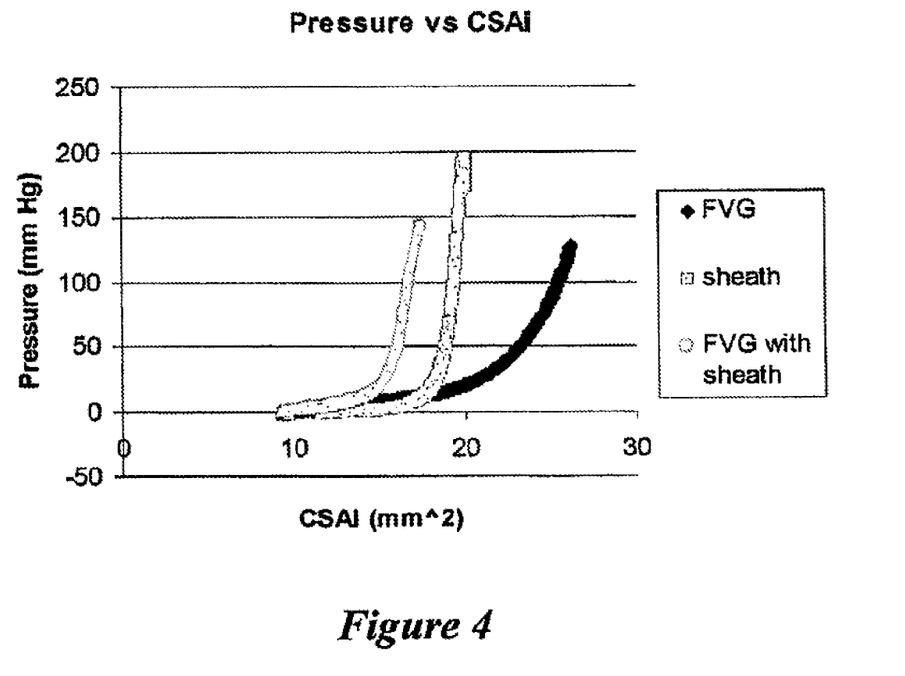
FIG. 4 shows a lumen cross-sectional area ($CSA_i$)-pressure relation for a femoral vein graft (FVG), the tissue engineer sheath and a combination of FVG surrounded by sheath.

FIG. 4 shows the pressure-$CSA_i$ (cross sectional area) relation for three different test samples: (1) an exemplary femoral vein graft (FVG); (2) sheath alone; and (3) femoral vein graft surrounded by sheath. Using each sample, an internal lumen pressure was applied to each sample and the resultant cross sectional area of the sample was measured in response to the application pressure. Results show that the engineered sheath has a similar pressure-$CSA_i$ shape as the vein graft except it is designed to have a smaller $CSA_i$ in response to a given applied pressure. The similar shape implies a similar stress-strain relation and hence similar mechanical properties. When the sheath is made to surround the vein graft, the graft will have a reduced diameter in response to applied pressure and hence reduced stress and strain. The majority of stress and strain is taken up by the wall of the sheath. In time, there is transfer of load from the sheath to the vein as the sheath resorbs and dilates. This gradual transfer of stress and strain reduces trauma and injury to the endothelial cells and vessel wall.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, the principles described above may be applied to various venous vessels other than the saphenous vein. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

The invention claimed is:

1. A vessel sheath, comprising:
   a first network comprising first fibers having a first resorption rate;
   a second network comprising second fibers having a second resorption rate; and
   a third network comprising third fibers having a third resorption rate, wherein the third resorption rate is slower than the second resorption rate;
   wherein said networks are positioned adjacent to one another and interwoven together to form a single sheath layer; and
   wherein said single sheath layer is configured so to form a tubular shape around a single axis;
   wherein all three networks of the single sheath layer are porous and are exposed to the same internal environment; and
   wherein when the sheath is externally wrapped around the vessel, the vessel is allowed to expand to the limits allowed by said networks of fibers and re-engineer itself according to a pressure within the vessel.

2. The vessel sheath of claim 1, wherein the second fibers and the third fibers comprise at least one waveform.

3. The vessel sheath of claim 1, wherein the second resorption rate is slower than the first resorption rate.

4. The vessel sheath of claim 3, wherein the first fibers comprise a straight configuration.

5. The vessel sheath of claim 1, wherein the first fibers are less distensible than the second fibers and the third fibers.

6. The vessel sheath of claim 1, wherein the first fibers are in a first sheath layer, wherein the second fibers are in a second sheath layer, and the third fibers are in a third sheath layer.

7. The vessel sheath of claim 6, wherein the first sheath layer is positioned between the vessel and the second sheath layer when the sheath is wrapped around the vessel.

8. The vessel sheath of claim 1, wherein the second fibers are thicker than the first fibers.

9. The vessel sheath of claim 8, wherein the third fibers are thicker than the second fibers.

10. A vessel sheath, comprising:
    a first network comprising first fibers having a first resorption rate;
    a second network comprising second fibers having a second resorption rate; and
    a third network comprising third fibers having a third resorption rate;
    wherein said networks are interwoven together to form a single sheath layer;
    wherein the sheath is externally wrapped around the vessel in a tubular structure;
    the tubular structure having a first diameter limit, a second diameter limit and a third diameter limit;
    the first diameter limit being smaller than the second diameter limit and the second diameter limit being smaller than the third diameter limit;
    wherein the tubular structure is at the first diameter limit when initially wrapped around the vessel;
    wherein the tubular structure is expandable to the second diameter limit when the first network is resorbed; and
    wherein the tubular structure is expandable to the third diameter limit when the second network is resorbed; and
    wherein the fibers of the three networks are cross-connected so as to limit the expansion of the fibers of the third network of the tubular structure to the first diameter limit and the second diameter limit;
    wherein the vessel is allowed to expand to the diameter limits allowed by said networks of fibers and re-engineer itself according to a pressure within the vessel.

11. The vessel sheath of claim 10, wherein the second resorption rate is slower than the first resorption rate.

12. The vessel sheath of claim 11, wherein the third resorption rate is slower than the second resorption rate.

13. The vessel sheath of claim 10, wherein the first fibers are in a first sheath layer, wherein the second fibers are in a second sheath layer, and the third fibers are in a third sheath layer.

14. The vessel sheath of claim 10, wherein said networks are positioned adjacent to one another.

15. A vessel sheath, comprising:
a first network comprising first fibers having a first resorption rate, a straight configuration, and a first thickness;
a second network comprising second fibers having a second resorption rate and a second thickness; and
a third network comprising third fibers having a third resorption rate and a third thickness and an initial wavy configuration;
wherein said networks are interwoven together to form a single sheath layer;
wherein the third resorption rate is slower than the second resorption rate, which is slower than the first resorption rate;
wherein the third thickness is thicker than the second thickness, which is thicker than the first thickness; and
wherein when the sheath is externally wrapped around the vessel in a tubular structure;
the tubular structure having a first diameter limit, a second diameter limit and a third diameter limit;
the first diameter limit being smaller than the second diameter limit and the second diameter limit being smaller than the third diameter limit;
wherein the tubular structure is at the first diameter limit when initially wrapped around the vessel;
wherein the tubular structure is expandable to the second diameter limit when the first network is resorbed; and
wherein the tubular structure is expandable to the third diameter limit when the second network is resorbed and due to the expansion of the third network due to the wavy configuration of the third fibers; and
the vessel is allowed to expand to the diameter limits allowed by said networks of fibers and re-engineer itself according to a pressure within the vessel.

16. The vessel sheath of claim 15, wherein said networks are positioned adjacent to one another.

* * * * *